United States Patent
Yamada

(10) Patent No.: US 10,091,989 B2
(45) Date of Patent: Oct. 9, 2018

(54) COMPOSITION FOR PEST CONTROL AEROSOL

(75) Inventor: Masahiro Yamada, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 13/820,801

(22) PCT Filed: Sep. 16, 2011

(86) PCT No.: PCT/JP2011/071775
§ 371 (c)(1),
(2), (4) Date: Mar. 5, 2013

(87) PCT Pub. No.: WO2012/036316
PCT Pub. Date: Mar. 22, 2012

(65) Prior Publication Data
US 2013/0171076 A1 Jul. 4, 2013

(30) Foreign Application Priority Data

Sep. 17, 2010 (JP) ................. 2010-209068

(51) Int. Cl.
*A01N 25/06* (2006.01)
*A01N 53/00* (2006.01)

(52) U.S. Cl.
CPC ............ *A01N 25/06* (2013.01); *A01N 53/00* (2013.01)

(58) Field of Classification Search
CPC ......... A01N 25/06; A01N 53/00; A01N 25/02
See application file for complete search history.

(56) References Cited

U.S. PATENT DOCUMENTS

| 5,190,745 | A | 3/1993 | Dohara et al. |
| 6,225,495 | B1 | 5/2001 | Ujihara et al. |
| 6,403,058 | B1 * | 6/2002 | Okada ................... A01N 47/40 424/405 |
| 7,776,792 | B2 * | 8/2010 | Maier et al. .................. 504/363 |
| 2006/0034931 | A1 * | 2/2006 | Hansen ......................... 424/486 |
| 2006/0182774 | A1 | 8/2006 | Fujii |

FOREIGN PATENT DOCUMENTS

| CN | 101406177 A | 4/2009 |
| CN | 101632380 A | 1/2010 |
| CN | 101637178 A | 2/2010 |
| EP | 0 128 351 A1 | 12/1984 |
| GB | 2 243 297 A | 10/1991 |
| JP | 59-212403 A | 12/1984 |
| JP | 4-120003 A | 4/1992 |
| JP | 5-286805 A | 11/1993 |
| JP | 10-194902 A | 7/1998 |
| JP | 11-308958 A | 11/1999 |
| JP | 2001-17055 A | 1/2001 |
| JP | 2001-342104 A | 12/2001 |
| JP | 2001342104 A * | 12/2001 ............ A01N 53/06 |
| JP | 2002-3302 A | 1/2002 |
| JP | 2002-68911 A | 3/2002 |
| JP | 2003-81721 A | 3/2003 |
| JP | 2003-160418 A | 3/2003 |
| JP | 3728967 B2 | 12/2005 |
| JP | 2006-117623 A | 5/2006 |
| JP | 2006-325489 A | 12/2006 |
| JP | 2007-1985 A | 1/2007 |
| JP | 2008-63242 A | 3/2008 |
| JP | 2010-065056 A | 3/2010 |
| WO | WO 2005/013685 A1 | 2/2005 |
| WO | WO 2006/111750 A1 | 10/2006 |
| WO | WO 2008/123574 A2 | 10/2008 |

OTHER PUBLICATIONS

The Patent Examination Report No. 1, dated Oct. 17, 2013, issued in the corresponding Australian Patent Application No. 2011302935.
International Preliminary Report on Patentability dated Mar. 19, 2013, for International Application No. PCT/JP2011/071775.
XP 002667144: Database WPI Week 200226 Thomson Scientific, London, GB, Dec. 11, 2001; AN 2002-199261.
XP 002667145: Database WPI Week 201023 Thomson Scientific, London, GB, Mar. 25, 2010; AN 2010-D22403.
XP 002667146: Database WPI Week 200377 Thomson Scientific, London, GB, Jun. 3, 2003; AN 2003-818766.
The Office Action (including an English translation), dated Mar. 6, 2015, issued in the corresponding Taiwanese Patent Application No. 100133455.
A Rejection Decision (including an English translation thereof) issued in the corresponding Taiwanese Patent Application No. 100133455 dated Aug. 7, 2015.
Communication pursuant to Article 94(3) EPC issued in the corresponding European Patent Application No. 11768180.9 dated Oct. 20, 2015.

(Continued)

*Primary Examiner* — Kyle A Purdy
(74) *Attorney, Agent, or Firm* — Birch, Stewart, Kolasch & Birch, LLP

(57) ABSTRACT

Technical Problem: To provide a composition for aerosol having an excellent pests control effect. Solution to Problem: A composition for pest control aerosol comprising; a compound of formula (1) wherein $R^a$ represents a hydrogen atom or a methyl group, $R^b$ represents a methyl group or a methoxymethyl group, an organic solvent having a boiling point of 220° C. or higher and a propellant, and the content of the organic solvent being 10 to 30 wt % of the total amount of the composition.

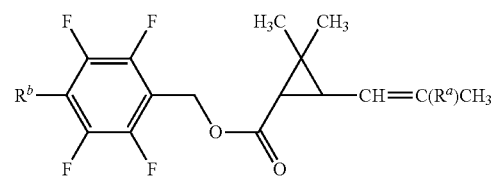

(1)

8 Claims, No Drawings

(56) References Cited

OTHER PUBLICATIONS

Office Action (including a partial English translation thereof) issued in the corresponding Indonesian Patent Application No. WO0201301139 dated Jun. 8, 2016.
Office Action and Search Report issued in the corresponding Malaysian Patent Application No. PI2013000643 dated Jul. 15, 2016.
European Office Action, dated Feb. 27, 2017, for European Application No. 11 768 180.9.
Brazilian Gazette dated Aug. 15, 2017, informing that an Unfavourable Opinion was drafted dated Aug. 4, 2017 in the corresponding Brazilian Patent Application No. BR 11 2013 005531-6 (including an English translation thereof).
European Office Action, dated Apr. 6, 2018, for corresponding European Application No. 11768180.9.
Brazilian Office Action, dated Dec. 5, 2017, for Brazilian Application No. 112013005531-6, with English translation.
Taiwanese Office Action, dated Sep. 21, 2016, for Taiwanese Application No. 100133455, along with an English translation.

* cited by examiner

COMPOSITION FOR PEST CONTROL AEROSOL

TECHNICAL FIELD

The present application is filed claiming the priority based on the Japanese Patent Application No. 2010-209068 (filed on Sep. 17, 2010), the entire content of which is incorporated herein by reference.

The present invention relates to a composition for a pest control aerosol.

BACKGROUND ART

It is known that a composition for a pest control aerosol containing [2,3,5,6-tetrafluoro-4-(methoxymethyl)phenyl]methyl=2,2-dimethyl-3-(1-propenyl)cyclopropanecarboxylate and a propellant has a pest control effect (see e.g. Patent Literature 1).

CITATION LIST

Patent Literature

Patent Literature 1: JP-A-2001-342104

SUMMARY OF INVENTION

Technical Problem

An object of the present invention is to provide a composition for an aerosol having an excellent pest control effect.

Solution to Problem

As a result of their intensive study to solve the problem, the present inventors found that a composition for a pest control aerosol containing a particular compound, a specified amount of an organic solvent having a specified range of a boiling point, and a propellant has an excellent pest control effect, to achieve the present invention.

The present invention provides:
[1] A composition for a pest control aerosol, the composition comprising;
a compound of formula (1)

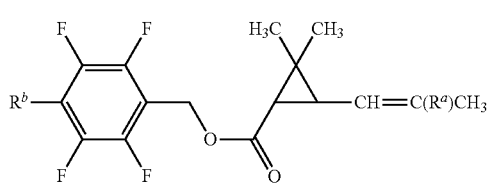

wherein
$R^a$ represents a hydrogen atom or a methyl group, and
$R^b$ represents a methyl group or a methoxymethyl group (hereinafter referred to as "present compound"),
an organic solvent having a boiling point of 220° C. or higher, and
a propellant, and
the content of the organic solvent being 10 to 30 wt % of the total amount of the composition.

[2] The composition according to item [1], wherein the content of the compound of formula (1) is 0.1 to 10 wt % of the total amount of the composition.
[3] The composition according to item [1] or [2], wherein the organic solvent is an ester solvent.
[4] The composition according to any one of items [1] to [3], wherein the organic solvent is an ester of 12 to 30 carbon atoms.
[5] The composition according to any one of items [1] to [4], wherein the organic solvent is one or more members selected from the group consisting of alkyl alkylcarboxylates of 12 to 30 carbon atoms, dialkyl dicarboxylates of 12 to 30 carbon atoms, trialkyl acetylcitrates of 12 to 30 carbon atoms, trialkyl citrates of 12 to 30 carbon atoms, and dialkyl phthalates of 12 to 30 carbon atoms.
[6] The composition according to any one of items [1] to [5], wherein the organic solvent is one or more members selected from the group consisting of dibutyl phthalate, isopropyl myristate, diisopropyl adipate, dioctyl adipate, diisononyl adipate, diisodecyl adipate, triethyl acetylcitrate, tributyl acetylcitrate, and triethyl citrate.
[7] The composition according to any one of items [1] to [6], which controls a flying pest.
[8] A pest control aerosol comprising the composition according to any one of items [1] to [7].
[9] A method for controlling pests, which comprises spraying an effective amount of the composition according to any one of items [1] to [7] to a pest, a path of the pest, and/or a habitat of the pest.

Effects of Invention

The composition of the invention has an excellent control effect on pests.

DESCRIPTION OF EMBODIMENTS

The present compounds include [2,3,5,6-tetrafluoro-4-(methoxymethyl)phenyl]methyl=2,2-dimethyl-3-(1-propenyl)cyclopropanecarboxylate (hereinafter referred to as "Compound A"), [2,3,5,6-tetrafluoro-4-methylphenyl]methyl=2,2-dimethyl-3-(1-propenyl)cyclopropanecarboxylate (hereinafter referred to as "Compound B"), and [2,3,5,6-tetrafluoro-4-(methoxymethyl)phenyl]methyl=2,2-dimethyl-3-(2-methyl-1-propenyl)cyclopropanecarboxylate (hereinafter referred to as "Compound C").

The present compounds are the compounds disclosed in JP-A-11-222463, JP-A-2000-63329, and JP-A-2001-11022, and can be prepared by the processes disclosed in the publications.

The present compounds may be present as isomers due to two asymmetric carbon atoms on the cyclopropane ring and the double bond. Any mixture containing active isomers at any ratio may be used for the present invention.

The content of the present compound contained in the composition of the invention is generally 0.1 to 10 wt % of the total amount of the composition.

The composition of the invention contains an organic solvent having a boiling point of 220° C. or higher. In view of persistence after the application, the organic solvent may be for example an ester solvent having a boiling point of 220° C. or higher, preferably from 220 to 500° C.

Herein the boiling point is shown as a value measured at atmospheric pressure.

The ester solvent is preferably an ester of 12 to 30 carbon atoms, and examples thereof include alkyl carboxylates of 12 to 30 carbon atoms, for example, alkyl alkylcarboxylates of 12 to 30 carbon atoms such as isopropyl myristate, hexyl laurate, and isopropyl palmitate; dialkyl dicarboxylates of 12 to 30 carbon atoms such as diisopropyl adipate, dioctyl adipate, isononyl adipate, and diisodecyl adipate; trialkyl acetylcitrates of 12 to 30 carbon atoms such as triethyl acetylcitrate and tributyl acetylcitrate; trialkyl citrates of 12 to 30 carbon atoms such as triethyl citrate; and dialkyl phthalates of 12 to 30 carbon atoms such as dibutyl phthalate and diisononyl phthalate.

More preferred examples of the ester solvent include alkyl alkylcarboxylates of 12 to 30 carbon atoms, dialkyl dicarboxylates of 12 to 30 carbon atoms, trialkyl acetylcitrates of 12 to 30 carbon atoms, trialkyl citrates of 12 to 30 carbon atoms, and dialkyl phthalates of 12 to carbon atoms. Alkyl alkylcarboxylates of 12 to 30 carbon atoms, dialkyl dicarboxylates of 12 to 30 carbon atoms, and trialkyl acetylcitrates of 12 to 30 carbon atoms are especially preferred.

Specific examples of the ester solvent include preferably dibutyl phthalate, isopropyl myristate, diisopropyl adipate, dioctyl adipate, isononyl adipate, diisodecyl adipate, triethyl acetylcitrate, tributyl acetylcitrate, and triethyl citrate, more preferably isopropyl myristate, diisopropyl adipate, dioctyl adipate, isononyl adipate, diisodecyl adipate, triethyl acetylcitrate, and tributyl acetylcitrate.

Other examples of the organic solvent having a boiling point of 220° C. or higher include saturated hydrocarbons such as straight-chain saturated hydrocarbons, branched saturated hydrocarbons, and alicyclic saturated hydrocarbons, and aromatic hydrocarbons, particularly Isopar M (a saturated hydrocarbon from ExxonMobil Yugen Kaisha, the boiling point: 223 to 254° C.), Isopar V (a saturated hydrocarbon from ExxonMobil Yugen Kaisha, the boiling point: 273 to 310° C.), IP Solvent 2835 (a saturated hydrocarbon from IDEMITSU KOSAN CO., LTD., the boiling point: 277 to 353° C.), Norpar 13 (a saturated hydrocarbon from ExxonMobil Yugen Kaisha, the boiling point: 222 to 242° C.), Norpar 15 (a saturated hydrocarbon from ExxonMobil Yugen Kaisha, the boiling point: 249 to 274° C.), Neothiozol (a saturated hydrocarbon from Chuo Kasei Co., Ltd, the boiling point: 225 to 247° C.), Exxsol D110 (a saturated hydrocarbon from ExxonMobil Yugen Kaisha, the boiling point: 249 to 267° C.), Exxsol D130 (a saturated hydrocarbon from ExxonMobil Yugen Kaisha, the boiling point: 279 to 313° C.), Alkene L (an aromatic hydrocarbon from Nippon Oil Corporation, the boiling point: 285 to 309° C.), Alkene 200P (an aromatic hydrocarbon from Nippon Oil Corporation, the boiling point: 321 to 390° C.), alkylidene carbonates such as ethylene carbonate and propylene carbonate, and glycol ethers such as diethylene glycol monobutyl ether and triethylene glycol monomethyl ether.

The content of the organic solvent having a boiling point of 220° C. or higher is 10 to 30 wt %. The organic solvent may be used alone or in combination of two or more.

The propellants contained in the composition of the invention include, for example, a nitrogen gas, a compressed air, a carbon dioxide gas, a liquefied petroleum gas (LPG), and dimethyl ether. The propellant contained in the composition of the invention may be used alone or in combination of two or more.

If necessary, one or more of other pest control agents, repellents, synergists, stabilizers and flavors may be conveniently contained in the composition of the invention.

The other pest control agents include, for example, organic phosphorus compounds such as dichlorvos, fenitrothion, tetrachlorvinphos, fenthion, chlorpyrifos, and diazinon; carbamate compounds such as propoxur, carbaryl, metoxadiazone, and fenobucarb; inhibitors of chitin formation such as lufenuron, chlorfluazuron, hexaflumuron, diflubenzuron, cyromazine, and 1-(2,6-difluorobenzoyl)-3-[2-fluoro-4-(1,1,2,3,3,3-hexafluoropropoxy)phenyl]urea; juvenile hormone-like agents such as pyriproxyfen, methoprene, hydroprene, and fenoxycarb; neonicotinoid compounds; and N-phenylpyrazole compounds.

The repellents include, for example, N,N-diethyl-m-toluamide, limonene, linalool, citronellal, menthol, menthone, hinokitiol, geraniol, eucalyptol, indoxacarb, carane-3,4-diol, MGK-R-326, MGK-R-874, and BAY-KBR-3023.

The synergists include, for example, 5-[2-(2-butoxyethoxy)ethoxymethyl]-6-propyl-1,3-benzodioxole, N-(2-ethylhexyl)bicyclo[2.2.1]hept-5-ene-2,3-dicarboxyimide, octachlorodipropyl ether, isobornyl thiocyanoacetate, and N-(2-ethylhexyl)-1-isopropyl-4-methylbicyclo[2.2.2]oct-5-ene-2,3-dicarboxyimide.

The stabilizers include, for example, phenolic antioxidants such as 2,6-di-t-butyl-4-methylphenol.

The composition of the invention can be prepared for example by mixing the present compound, the organic solvent, and the propellant, and, if necessary the other pest control agent, a repellent, a synergist, a stabilizer, a flavor, or the like.

The pest control aerosol of the invention contains the composition of the invention. In such pest control aerosol, the composition of the invention is usually contained in an aerosol device. The aerosol devices are generally equipped with a pressure vessel containing the composition and the like to be sprayed in the form of a mist with the aid of pressure of a propellant.

The pest control aerosol can be prepared for example by charging an aerosol vessel with the present compound and the organic solvent, and, if necessary, the other pest control agent, a repellent, a synergist, a stabilizer, a flavor, or the like; attaching an aerosol valve to the vessel; filling the vessel with the propellant via a stem; shaking the vessel; and attaching an actuator to the vessel. The aerozol valves include, but are not limited to, push down-type valves. The actuators include, for example, button-type or trigger-type actuators.

The pest control method of the invention is carried out by spraying an effective amount of the composition of the invention to a pest, a path of the pest and/or a habitat of the pest. In particular, it is carried out by spraying the composition of the invention to the pest, a path of the pest and/or a habitat of the pest through the use of the pest control aerosol containing the composition of the invention. For practical purposes, it is advantageous to spray the composition of the invention to a space to be pest-controlled. In such a case, the amount of the present compound to be sprayed is usually 0.001 to 1000 $mg/m^3$, preferably 0.001 to 100 $mg/m^3$, more preferably 0.01 to 10 $mg/m^3$ in terms of the total amount of the present compound. When applied to a plane, the amount is 0.0001 to 1000 $mg/m^2$ in terms of the total amount of the present compound. Examples of the space where the composition of the invention is sprayed include room interiors, living rooms, dining rooms, wardrobes, closets, chests such as Japanese chest, cupboards, toilets, bathrooms, storerooms, warehouses, and car interiors. Furthermore, the composition can also be sprayed to outside open space.

Examples of the pests which can be controlled by the composition of the invention include arthropods such as insects and acarian, particularly the following pests may be mentioned.

Lepidoptera:
Pyralidae such as *Chilo suppressalis, Cnaphalocrocis medinalis*, and *Plodia interpunctella*; Hadeninae such as *Spodoptera litura, Mythimna separate*, and *Mamestra brassicae*; Pieridae such as *Pieris rapae*; Tortricidae such as *Adoxophyes* spp.; Carposinidae; Lyonetiidae; Lymantriidae; Plusinae; *Agrotis* spp. such as *Agrotis segetum* and *Agrotis ipsilon*; and *Helicoverpa* spp., *Heliothis* spp., *Plutella xylostella, Parnara guttata, Tinea translucens*, and *Tineola bisselliella*, etc.

Diptera:
*Culex* spp. such as *Culex pipiens pallens, Culex tritaeniorhynchus*, and *Culex pipiens quinquefasciatus; Aedes* spp. such as *Aedes aegypti* and *Aedes albopictus*; Anophelinae such as *Anopheles sinensis* and *Anopheles gambiae*; Chironomidae; Muscidae such as *Musca domestica, Muscina stabulans*, and *Fannia canicularis*; Calliphoridae; Sarcophagidae; Anthomyiidae such as *Delia platura* and *Delia antique*; Tephritidae; Drosophilidae; Psychodidae; Phoridae; Tabanidae; Simuliidae; Stomoxyini; and Ceratopogonidae, etc.

Dictyoptera:
*Blattella germanica, Periplaneta fuliginosa, Periplaneta Americana, Periplaneta australasiae, Periplaneta brunnea Burmeister*, and *Blatta orientalis*, etc.

Hymenoptera:
Formicidae; Polistinae such as *Polistes chinensis, Polistes riparius, Polistes jadwigae, Polistes rothneyi, Polistes mandarinus, Polistes snelleni*, and *Polistes japonicus*; Vespinae such as *Vespa mandarinia, Vespa simillima xanthoptera, Vespa analis, Vespa crabro, Vespa ducalis, Vespula flaviceps, Vespula shidai*, and *Dolichovespula media*; Bethylidae; Xylocopa; Pompilidae; Sphecidae; and Eumenidae, etc.

Siphonaptera:
*Ctenocephalides canis, Ctenocephalides felis*, and *Pulex irritans*, etc.

Anoplura:
*Pediculus humanus, Phthirus pubis, Pediculus humanus humanus*, and *Pediculus humanus corporis*, etc.

Isoptera:
*Reticulitermes speratus* and *Coptotermes formosanus*, etc.

Hemiptera:
Delphacidae such as *Laodelphax striatellus, Nilaparvata lugens*, and *Sogatella furcifera*; Deltocephalidae such as *Nephotettix cincticeps* and *Nephotettix virescens*; Aphidoidea; Pentatomidae; Aleyrodidae; Coccoidea; Tingidae; Psyllidae; and Cimicidae, etc.

Coleoptera:
*Attagenus japonicus, Anthrenus verbasci; Diabrotica* spp. such as *Diabrotica virgifera virgifera* and *Diabrotica undecimpunctata howardi*; Scarabaeidae such as *Anomala cuprea* and *Anomala rufocuprea*; Curculionoidea such as *Sitophilus zeamais, Lissorhoptrus oryzophilus, Anthonomus grandis*, and *Callosobruchus chinensis*; Tenebrionidae such as *Tenebrio molitor* and *Tribolium castaneum*; Chrysomelidae such as *Oulema oryzae, Phyllotreta striolata*, and *Aulacophora femoralis; Anobiidae; Epilachna* spp. such as *Epilachna vigintioctopunctata*; Lyctinae; Bostrychidae; Cerambycidae; *Paederus fuscipes*, etc.

Thysanoptera:
*Thrips palmi, Frankliniella occidentalis*, and *Thrips hawaiiensis*, etc.

Orthoptera:
Gryllotalpidae and Caelifera etc.

Acari:
Pyroglyphidae such as *Dermatophagoides farinae* and *Dermatophagoides pteronyssinus*; Acaridae such as *Tyrophagus putrescentidae* and *Aleuroglyphus ovatus*; Glycyphagidae such as *Glycyphagus privates, Glycyphagus domesticus*, and *Glycyphagus destructor*; Cheyletidae such as *Cheyletus malaccensis* and *Cheyletus fortis*; Tarsonemidae; Chortoglyphidae; Haplochthoniidae; Tetranychidae such as *Tetranychus urticae, Tetranychus kanzawai, Panonychus citri*, and *Panonychus ulmi*; Ixodidae such as *Haemaphysalis longicornis*, etc.

The compositions of the invention are especially effective to control so-called flying pests, for example mosquitoes and flies classified as Diptera and bees classified as Hymenoptera.

EXAMPLES

Hereinafter, the present invention is described specifically by way of formulation examples and test examples to which the present invention is not limited.

First, some formulation examples of the aerosol containing the composition of the invention are described. The term "part(s)" means part(s) by weight.

Preparation Example 1

Into an aerosol can 4.3 parts of Compound A and 10.0 parts of dibutyl phthalate are charged, a valve part is attached to the can, and the can is filled with 85.7 parts of a propellant (liquefied petroleum gas) via the valve part to give Aerosol 1 containing 100 parts of the composition of the invention.

Preparation Example 2

Into an aerosol can 4.3 parts of Compound A and 30.0 parts of dibutyl phthalate are charged, a valve part is attached to the can, and the can is filled with 65.7 parts of a propellant (liquefied petroleum gas) via the valve part to give Aerosol 2 containing 100 parts of the composition of the invention.

Preparation Examples 3 and 4

Aerosols 3 and 4 are prepared analogously to the process described under Preparation Examples 1 and 2, except that isopropyl myristate is employed in place of dibutyl phthalate.

Preparation Examples 5 and 6

Aerosols 5 and 6 are prepared analogously to the processes described under Preparation Examples 1 and 2, except that diisopropyl adipate is employed in place of dibutyl phthalate.

Preparation Examples 7 and 8

Aerosols 7 and 8 are prepared analogously to the processes described under Preparation Examples 1 and 2, except that dioctyl adipate is employed in place of dibutyl phthalate.

Preparation Examples 9 and 10

Aerosols 9 and 10 are prepared analogously to the processes described under Preparation Examples 1 and 2, except that diisononyl adipate is employed in place of dibutyl phthalate.

Preparation Examples 11 and 12

Aerosols 11 and 12 are prepared analogously to the processes described under Preparation Examples 1 and 2, except that diisodecyl adipate is employed in place of dibutyl phthalate.

Preparation Examples 13 and 14

Aerosols 13 and 14 are prepared analogously to the processes described under Preparation Examples 1 and 2, except that triethyl acetylcitrate is employed in place of dibutyl phthalate.

Preparation Examples 15 and 16

Aerosols 15 and 16 are prepared analogously to the processes described under Preparation Examples 1 and 2, except that tributyl acetylcitrate is employed in place of dibutyl phthalate.

Preparation Examples 17 and 18

Aerosols 17 and 18 are prepared analogously to the processes described under Preparation Examples 1 and 2, except that triethyl citrate is employed in place of dibutyl phthalate.

Preparation Examples 19 and 20

Aerosols 19 and 20 are prepared analogously to the processes described under Preparation Examples 1 and 2, except that Isopar M (from ExxonMobil Yugen Kaisha) is employed in place of dibutyl phthalate.

Preparation Examples 21 and 22

Aerosols 21 and 22 are prepared analogously to the processes described under Preparation Examples 1 and 2, except that Norpar 13 (from ExxonMobil Yugen Kaisha) is employed in place of dibutyl phthalate.

Preparation Examples 23 and 24

Aerosols 23 and 24 are prepared analogously to the processes described under Preparation Examples 1 and 2, except that Exxsol D110 (from ExxonMobil Yugen Kaisha) is employed in place of dibutyl phthalate.

Preparation Examples 25 and 26

Aerosols 25 and 26 are prepared analogously to the processes described under Preparation Examples 1 and 2, except that Alkene L (from Nippon Oil Corporation) is employed in place of dibutyl phthalate.

Preparation Examples 27 and 28

Aerosols 27 and 28 are prepared analogously to the processes described under Preparation Examples 1 and 2, except that propylene carbonate is employed in place of dibutyl phthalate.

Preparation Examples 29 and 30

Aerosols 29 and 30 are prepared analogously to the processes described under Preparation Examples 1 and 2, except that diethylene glycol monobutyl ether is employed in place of dibutyl phthalate.

Preparation Example 31

Into an aerosol can (product name: AE180WON, from TOYO SEIKAN KAISHA, LTD) 4.3 parts of Compound A and 13.6 parts of isopropyl myristate were charged, a push down-type valve with a stem having a pore size of 0.33 mm was attached to the can, and the can was filled with 82.1 parts of a propellant (liquefied petroleum gas) via the valve part to give Aerosol 31 containing 100 parts of the composition of the invention.

Preparation Example 32

Aerosol 32 was prepared analogously to the process described under Preparation Example 31, except that propylene carbonate was employed in place of isopropyl myristate.

Preparation Example 33

Into an aerosol can 1.2 parts of Compound A and 30.0 parts of dibutyl phthalate were charged, a valve part was attached to the can, and the can was filled with 68.8 parts of a propellant (liquefied petroleum gas) via the valve part to give Aerosol 33 containing 100 parts of the composition of the invention.

Preparation Example 34

Aerosol 34 was prepared analogously to the process described under Preparation Example 33, except that isopropyl myristate was employed in place of dibutyl phthalate.

Preparation Example 35

Into an aerosol can 1.2 parts of Compound A and 10.0 parts of isopropyl myristate were charged, a valve part was attached to the can, and the can was filled with 88.8 parts of a propellant (liquefied petroleum gas) via the valve part to give Aerosol 35 containing 100 parts the composition of the invention.

Preparation Examples 36 to 70

Aerosols 36 to 70 are prepared analogously to the processes described under Preparation Examples 1 to 35, except that Compound B is employed in place of Compound A.

Preparation Examples 71 to 105

Aerosols 71 to 105 are prepared analogously to the processes described under Preparation Examples 1 to 35, except that Compound C is employed in place of Compound A.

Preparation Example 106

Into an aerosol can (product name: AE180WON, from TOYO SEIKAN KAISHA, LTD) 4.3 parts of Compound A and 27.2 parts of isopropyl myristate were charged, a push down-type valve with a stem having a pore size of 0.33 mm was attached to the can, the can was filled with 68.5 parts of a propellant (liquefied petroleum gas) via the valve part to give Aerosol 106 containing 100 parts of the composition of the invention.

Comparison Preparation Example 1

Into an aerosol can (product name: AE180WON, from TOYO SEIKAN KAISHA, LTD) 4.3 parts of Compound A and 17.4 parts of ethanol were charged, a push down-type valve with a stem having a pore size of 0.33 mm was attached to the can, the can was filled with 77.8 parts of a propellant (liquefied petroleum gas) via the valve part to give Comparison Aerosol 1.

Comparison Preparation Example 2

Into an aerosol can (product name: AE180WON, from TOYO SEIKAN KAISHA, LTD) 4.3 parts of Compound A and 6.8 parts of isopropyl myristate were charged, a push down-type valve with a stem having a pore size of 0.33 mm was attached to the can, the can was filled with 88.9 parts of a propellant (liquefied petroleum gas) via the valve part to give Comparison Aerosol 2.

Comparison Preparation Example 3

Into an aerosol can (product name: AE180WON, from TOYO SEIKAN KAISHA, LTD) 4.3 parts of Compound A and 54.4 parts of isopropyl myristate were charged, a push down-type valve with a stem having a pore size of 0.33 mm was attached to the can, the can was filled with 41.3 parts of a propellant (liquefied petroleum gas) via the valve part to give Comparison Aerosol 3.

The following test examples show that the compositions of the invention and the aerosols containing the composition of the invention have an excellent pest control effect.

In the following test examples, [2,3,5,6-tetrafluoro-4-(methoxymethyl)phenyl]methyl=(1R)-trans-2,2-dimethyl-3-(1-propenyl(E/Z=1/8))cyclopropanecarboxylate was employed as Compound A. In addition, in the following test examples, all aerosols were equipped with a button-type actuator having a nozzle size of 0.41 mm.

Test Example 1

About 0.11 g of the composition of the invention was sprayed to a cuboid test chamber (28 m³) having dimensions of 3.0 m×4.0 m×2.3 m through the use of Aerosol 31. The composition was sprayed once from the entrance of the chamber toward the center, and then the chamber was closed. After 8 hours from the spraying, 100 adults of female *Culex pipiens pallens* were put into the chamber. After 2, 3, 5, 7, 10 and 15 minutes, the number of knock-down *Culex pipiens pallens* was counted, and KT50 (the time necessary to knock down 50% of the tested mosquitoes) was determined from the obtained data. The tests were carried out in the same manner as above for Aerosol 106 and Comparison Aerosols 1, 2 and 3.

The results are shown in Table 1.

TABLE 1

|  | KT50 (min) |
| --- | --- |
| Aerosol 31 | 5.5 |
| Aerosol 106 | 5.4 |

TABLE 1-continued

|  | KT50 (min) |
| --- | --- |
| Comparison Aerosol 1 | >30 |
| Comparison Aerosol 2 | >30 |
| Comparison Aerosol 3 | >30 |

Test Example 2

Aerosols 5, 9, 15 and 17 were prepared according to the processes described under Preparation Examples 5, 9, 15 and 17. The aerosol can and valve used in Preparation Example 31 were employed for these aerosols, and a button-type actuator having a nozzle size of 0.41 mm was attached thereto.

About 20 mg of the composition of the invention was sprayed to a cubic chamber having each edge length of 70 cm through the use of Aerosol 5. The composition was sprayed once from the window at the center of the near side of the chamber toward the center of the chamber, and then the chamber was closed. After 14 hours from the spraying, 20 adults of female *Culex pipiens pallens* were put into the chamber. After 2, 3, 5, 7, 10 and 15 minutes, the number of knock-down *Culex pipiens pallens* was counted, and KT50 (the time necessary to knock down 50% of the tested mosquitoes) was determined from the obtained data. The tests were carried out in the same manner as above for Aerosols 9, 15 and 17.

The results are shown in Table 2.

TABLE 2

|  | KT50 (min) |
| --- | --- |
| Aerosol 5 | 3.0 |
| Aerosol 9 | 5.5 |
| Aerosol 15 | 4.0 |
| Aerosol 17 | 5.0 |

INDUSTRIAL AVAILABILITY OF INVENTION

The composition of the invention has an excellent pest control effect.

The invention claimed is:
1. A method for controlling flying pests, which comprises spraying an effective amount of the composition comprising:
   a compound of formula (1)

$$R^b - \text{[2,3,5,6-tetrafluorophenyl-CH}_2\text{-O-C(=O)-C(CH}_3)_2\text{-CH=C(R}^a)\text{CH}_3\text{]} \quad (1)$$

wherein
$R^a$ represents a hydrogen atom or a methyl group, and
$R^b$ represents a methyl group or a methoxymethyl group,
an organic solvent having a boiling point of 220° C. or higher and
a propellant, and
the content of the organic solvent being 10 to 30 wt % of the total amount of the composition, wherein the organic solvent is one or more members comprising isopropyl myristate, to a flying pest, a path of the pest and/or a habitat of the pest.

2. The method according to claim 1, wherein the flying pest is a mosquito or a fly.

3. The method according to claim 1, wherein the flying pest is a mosquito.

4. The method according to claim 2, wherein the method is carried out by spraying a space to be flying pest-controlled.

5. The method according to claim 1, wherein $R^a$ is a hydrogen atom and, $R^b$ is a methoxymethyl group.

6. The method according to claim 5, wherein the flying pest is a mosquito or a fly.

7. The method according to claim 5, wherein the flying pest is a mosquito.

8. The method according to claim 5, wherein the method is carried out by spraying a space to be flying pest-controlled.

* * * * *